United States Patent
Lyles

(10) Patent No.: US 7,011,841 B2
(45) Date of Patent: Mar. 14, 2006

(54) HIGH DENSITY POROUS MATERIALS

(75) Inventor: Mark B. Lyles, 9127 Cap Mountain Dr., San Antonio, TX (US) 78255

(73) Assignee: Mark B. Lyles, San Antonio, TX (US)

( * ) Notice: Subject to any disclaimer, the term of this patent is extended or adjusted under 35 U.S.C. 154(b) by 159 days.

(21) Appl. No.: 09/817,010

(22) Filed: Mar. 24, 2001

(65) Prior Publication Data

US 2001/0044159 A1 Nov. 22, 2001

Related U.S. Application Data

(60) Provisional application No. 60/192,112, filed on Mar. 24, 2000.

(51) Int. Cl.
*A61K 9/00* (2006.01)
*A61K 6/00* (2006.01)
(52) U.S. Cl. ...................................... 424/422; 424/400
(58) Field of Classification Search ................ 424/400, 424/422
See application file for complete search history.

(56) References Cited

U.S. PATENT DOCUMENTS

| | | | |
|---|---|---|---|
| 5,621,035 A | * | 4/1997 | Lyles et al. .................. 433/226 |
| 5,629,186 A | | 5/1997 | Yasukawa et al. |
| 5,780,281 A | | 7/1998 | Yasukawa et al. |
| 5,843,767 A | | 12/1998 | Beattie |
| 5,951,295 A | * | 9/1999 | Lyles et al. ............... 433/228.1 |
| 5,964,745 A | | 10/1999 | Lyles et al. |
| 6,063,395 A | * | 5/2000 | Markkula et al. ........... 424/422 |

* cited by examiner

*Primary Examiner*—Thurman K. Page
*Assistant Examiner*—Simon J. Oh
(74) *Attorney, Agent, or Firm*—Baker Botts L.L.P.

(57) ABSTRACT

Porous materials are disclosed having densities of at least about 6 pounds per cubic foot (96.1 kg/m$^3$). The materials comprise silica and/or alumina.

The porous materials are useful as supports for binding various chemical and biological molecules. The materials are useful as supports for analytical processes such as ELISA, blotting, and hybridization assays. The materials can be used as reinforcement agents for organic, inorganic, or metallic materials.

13 Claims, No Drawings

HIGH DENSITY POROUS MATERIALS

This application claims the benefit of Provisional App. No. 60/192,112, filed Mar. 24, 2000.

FIELD OF THE INVENTION

The invention relates to porous materials and, more specifically, to porous silica materials. The materials are useful for the binding of chemical and biological molecules to be used in various analytical methods.

BACKGROUND OF THE INVENTION

Various plastic, glass, and membrane materials have historically been used to bind chemical and biological molecules for use in various analytic methods such as ELISA, Western blotting, and hybridizations.

These materials are limited by their relatively low loading potential, and by their non-porous nature.

U.S. Pat. No. 5,951,295 (issued Sep. 14, 1999) describes ceramic fused fiber enhanced dental materials, and methods for their preparation. Fused-fibrous material was taught comprising from about 1% to about 50% by weight alumina, from about 50% to about 98% silica, and from about 1% to about 5% by weight boron.

U.S. Pat. No. 5,964,745 (issued Oct. 12, 1999) describes an implantable system for bone or vascular tissue. The system comprises porous linked fibrous biomaterial manufactured from nonwoven, randomly-oriented fibers linked together using a fusion source at a plurality of cross-points into a porous structure, said biomaterial having a plurality of voids of a predetermined mean void size effective for stimulating angiogenesis in said biomaterial from the tissue or bone.

U.S. Pat. No. 5,621,035 (issued Apr. 15, 1997) describes filler compositions and ceramic enhanced dental materials. The preferred embodiment of the filler composition and the ceramic dental restorative material is comprised of about 22% by weight alumina, about 78% by weight silica, about 2% by weight silicon carbide, and about 2.85% by weight boron nitride with less than 1% cristobalite contamination.

Porous materials have been suggested by Yasukawa et al. (U.S. Pat. Nos. 5,629,186 and 5,780,281). A composite was prepared from silica and/or alumina fibers with added boron nitride. The composites were suggested as being useful for cell cultures, implants, and chromatography matrices.

There exists a need for materials which bind chemical and biological molecules while having improved surface properties.

SUMMARY OF THE INVENTION

Porous materials suitable for the binding of chemical and biological molecules are disclosed. The three dimensional properties of the materials results in improved loading properties. The materials can be used in a wide array of chemical and biological assays to improve sensitivities.

DETAILED DESCRIPTION OF THE INVENTION

Porous materials

A preferred embodiment of the invention is directed towards porous materials having densities of about 6 pounds per cubic foot (96.1 kg/m$^3$) and higher, about 8 pounds per cubic foot (128 kg/m$^3$) and higher, about 12 pounds per cubic foot (192 kg/m$^3$) and higher, about 24 pounds per cubic foot (384 kg/m$^3$) and higher, about 36 pounds per cubic foot (577 kg/m$^3$) and higher, about 48 pounds per cubic foot (769 kg/m$^3$) and higher, or about 64 pounds per cubic foot (1025 kg/m$^3$) and higher. The materials can comprise up to about 100% silica, or up to about 60% alumina. The silica can be up to about 50% cristobalite, up to about 75% cristobalite, up to about 90% cristobalite, up to about 95% cristobalite, up to about 99% cristobalite, or can be about 100% cristobalite. The alumina can be aluminum borosilicate.

The exposed surface of the materials ("surface chemistry") can be at least about 50% silicon dioxide, at least about 75% silicon dioxide, at least about 90% silicon dioxide, at least about 95% silicon dioxide, at least about 99% silicon dioxide, or can be about 100% silicon dioxide.

The materials can comprise other metal oxides in addition to or in place of the silica. For example, tantalum oxide or zirconium oxide can be incorporated into the materials.

The mean pore diameter of the materials can be less than 0.01 microns, about 0.1 micron to about 5 microns, up to about 10 microns, up to about 20 microns, up to about 30 microns, up to about 40 microns, up to about 50 microns, up to about 100 microns, up to about 200 microns, up to about 300 microns, up to about 400 microns, up to about 500 microns, or up to about 600 microns. Ranges of pore diameter include about 0.1 microns to about 1 micron, about 5 microns to about 10 microns, about 20 microns to about 50 microns, about 100 to about 400 microns, or about 200 microns to about 600 microns.

The surface properties of the materials can be modified by chemical reactions. Examples include modifying the hydrophobicity or hydrophilicity of the porous materials, and hydroxylation with phosphoric acid.

The materials can be reinforced using an additional silica gel

The materials can further comprise carbon fiber, organic fibers containing carbon, or other polymer materials.

Preparation of Porous Materials

The preparation of porous materials is generally described in U.S. Pat. No. 5,951,295 (issued Sep. 14, 1999).

Porous materials can be prepared from: (1) from about 1% to about 50% by weight alumina; (2) from about 50% to about 98% by weight silica; and (3) from about 1% to about 5% by weight boron. In addition, the composition can further comprise silicon carbide up to about 3% by weight. The materials can comprise over 99% silica.

Generally, the process for preparing the porous materials can comprise the following steps (as described in U.S. Pat. No. 5,951,295):

(1) preparation of a slurry mixture comprised of pre-measured amounts of purified fibers/materials and deionized water;
(2) removal of shot from slurry mixture;
(3) removal of water after thorough mixing to form a soft billet;
(4) addition of a ceramic binder after the formation of the billet;
(5) placement of the billet in a drying microwave oven for moisture removal; and
(6) sintering the dry billet in a large furnace at about 1600° F. or above.

The high purity silica fibers above are first washed and dispersed in hydrochloric acid and/or deionized water or other solvents. The ratio of washing solution to fiber is between 30 to 150 parts liquid (pH 3 to 4) to 1 part fiber. Washing for 2 to 4 hours generally removes the surface chemical contamination and non-fibrous material (shot) which contributes to silica fiber devitrification. After washing, the fibers are rinsed 3 times at approximately the same liquid to fiber ratio for 10 to 15 minutes with deionized water. The pH is then about 6. Excess water is drained off leaving a ratio of 5 to 10 parts water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 parts water with 1 part fiber in a V-blender for 2 1/2 to 5 minutes. The time required is a function of the fiber length and diameter. In general, the larger the fiber, the more time required.

Generally, in order to manufacture low density porous materials, for example, densities below 12 lb/ft$^3$ ((192 kg/m$^3$)), the process includes the additional steps of:

(1) the addition of expendable carbon fibers in the casting process and/or other temporary support material; and (2) firing the billet at about 1300° F. to remove the carbon fibers or other support material prior to the final firing at approximately 1600° F. or above.

When the dispersed silica fibers and dispersed alumina fibers are combined, the pH may be acidic, and if so, should be adjusted to neutral with ammonium hydroxide. The slurry should contain about 12 to about 25 parts water to about 1 part fiber. The slurry is mixed to a uniform consistency in a V-blender in 5 to 20 minutes. The boron nitride can be added at this point (2.85% by weight of the fibers) and mixed to a uniform consistency in a V-blender for an additional 5 to 15 minutes creating a Master Slurry. The preferred mixing procedure uses 15 parts water to 1 part fiber and the slurry is produced in about 20 minutes of mixing. At lower density formulations, expendable carbon fibers are used to give "green" strength to the billet prior to the final sintering. The percent of carbon fiber used varies greatly depending on the diameter, length and source of the fiber and the ultimate density of the material being produced. The percent of carbon fiber per dry weight of material should range between 1% and 10%. The source of the carbon fiber can take many forms including nylon, cellulose, and purified graphite based carbon in fibrous form. Carbon fibers added in the casting process are eliminated by firing the billets at 1350° F. prior to the final firing at 2450° F.

The Master Slurry is poured into a mold for pressing into the desired shape. The water is withdrawn rapidly and the resulting felt is compressed at 10 to 20 psi. Rapid removal of the water is required to prevent the fibers from separating. If graded properties are desired in the resultant material, the slurry can be allowed to settle and the fibers to partially separate before the removal of the water.

The final density of the finished restorative material is determined in part by the amount of compression placed on the felt, varying the wet molded dimension in relation to the fiber content. The formulation of the present invention has been prepared in densities ranging from about 0.05 to 0.48 g/cc. It can, however, be prepared in lower and higher densities.

After molding, the restorative material can be dried and fired by the following procedure. The material is first dried in an oven for 18 hours; the temperature, initially 38° C., is raised at a rate of 11° C. per hour to 104° C., held there for 4 hours, raised again at a rate of 11° C. per hour to 150° C., and held there for 4 hours. The material is taken directly from the drying oven, placed in the firing furnace, and fired. A temperature rise rate of 220° C. per hour or less is required in order to avoid cracking and warping in the case of a 15 cm×15 cm×7.5 cm block of material. For larger blocks, slower heating rates may be required. The maximum firing temperature may vary from 1200° C. to 1600° C. depending upon the fiber ratio used, amount of boron nitride, and the final density of the material that is desired.

The temperature rise rate is chosen to permit relatively uniform temperatures to be achieved throughout the material during the process. A faster temperature rise rate causes non-uniform temperatures to be achieved throughout the material during the process. A faster temperature rise rate causes nonuniform strength and density and may cause cracking. Longer or higher temperature firing results in higher shrinkage and related greater resistance to subsequent shrinkage, as well as a shorter lifetime to devitrification under cyclic exposures to high temperatures. The maximum firing temperature is dependent upon the fiber ratio used and the density of the composite desired. The firing time and maximum temperature are selected to allow sufficient shrinkage to achieve stabilization and fiber fusion while not allowing any devitrification. After firing, the material may be machined to obtain any desired final dimensions.

The following method of preparing the porous material, and several proposed uses, was described in U.S. Pat. No. 5,629,186.

Preparing the Matrix

In general, the method includes forming a fiber slurry having desired viscosity and fiber dispersion characteristics, allowing the slurry to settle under conditions that produce a selected fiber density and orientation, drying the resulting fiber block, and sintering the block to form the desired fused-fiber matrix.

A. Fiber Treatment

The silica ($SiO_2$) and/or alumina ($Al_2O_3$) fibers used in preparing the matrix are available from a number of commercial sources, in selected diameters (fiber thicknesses) between about 0.5 μm–20 μm. A preferred silica fiber is a high purity, amorphous silica fiber (99.7% pure), such as fabricated by Manville Corporation (Denver, Colo.) and sold under the fiber designation of "Q-fiber". High purity alumina fibers (average 3 microns) may be procured, for example, from ICI Americas, Inc. (Wilmington, Del.).

In a preferred heat treatment, the silica fibers are compressed into panels, e.g., using a Torit Exhaust System and compaction unit. The compressed panels are sent passed through a furnace, e.g., a Harper Fuzzbelt furnace or equivalent at 2200° F. for 120 minutes, corresponding to a speed setting of about 2.7 inches/minute. The heat treatment is used to close up surface imperfections on the fiber surfaces, making the matrix more stable to thermal changes on sintering. The heat treatment also improves fiber chopping properties, reducing fabrication time.

In a preferred method, the heat-treated fibers are washed to remove debris and loose particles formed during fiber manufacturing.

B. Preparing a Fiber Slurry

Silica and/or alumina fibers from above are blended to form a fiber slurry that is used in forming a "green-state" block that can be sintered to form the desired matrix.

The slurry is formed to contain, in an aqueous medium, silica, alumina, or silica and alumina fibers of the type described above, at a fiber:liquid weight ratio of between about 1:25 to 1:70, where the liquid weight refers to the liquid weight of the final slurry preparation.

The slurry preferably includes a thickening agent effective to give the slurry a viscosity between about 1,000 and 25,000 centipoise, as measured by standard methods. The viscosity agent may be any of a number of well-known hydrophilic polymers, such as polyvinylalcohol, polyvinylacetate, polyvinylpyrrolidone, polyurethane, polyacrylamide, food thickeners, such as gum arabic, acacia, and guar gum, and methacrylate type polymers. The polymers preferably have molecular weights greater than about 25–50 Kdaltons, and are effective to increase solution viscosity significantly at concentrations typically between about 0.5–10 weight percent solution.

Preferred thickening agents polymers that also have tacky or adhesive properties, such as methyl cellulose, terpolymers of maleic anhydride, alkyl vinyl ether, and an olefin (U.S. Pat. No. 5,034,486), copolymers of ethylene and olefins (U.S. Pat. No. 4,840,739), cellulose-containing pastes (U.S. Pat. No. 4,764,548), and soy polysaccharides. One preferred thickening agent is methylcellulose, e.g., the polymer sold under the tradename Methocel A4M and available from Dow Chemical Co. (Midland, Mich.).

Where the matrix is formed of high-purity silica fibers and/or alumina, the slurry is also formed to contain a source of boron that functions, during sintering, to form a boron/silica or boron/alumina surface eutectic that acts to lower the melting temperature of the fibers, at their surfaces, to promote fiber/fiber fusion at the fiber intersections. In a preferred embodiment, the boron is supplied in the slurry as boron nitride particles 15 to 60 $\mu$m in size particles. Such particles can be obtained from Carborundum (Amherst, N.Y.). The amount of boron nitride is preferably present in the slurry in an amount constituting between about 2–12 weight percent of the total fiber weight.

The adhesive property of the thickening agent described above is useful in adhering particles of boron nitride and, if used, silicon carbide, to the fibers in the slurry, to produce a relatively uniform of particles in the slurry, and prevent the particles from settling out of slurry during the molding process described below.

The slurry preferably also contains a dispersant which acts to coat the fibers and help disperse the fibers, both to increase slurry viscosity, and to prevent silica fibers from "bundling" and settling out of the slurry as fiber aggregates during the molding process described below. The dispersant is preferably one which imparts a significant charge and/or hydrophilicity to the fibers, to keep the fibers separated during slurry formation and settling during the molding process.

For use with silica fibers, ammonium salts are particularly useful as dispersants, because the ammonium cation is released from the matrix in the form of ammonia during matrix drying and/or sintering. Preferred ammonium salts are the salts of polyanionic polymers, such as ammonium polymethylmethacrylate, or the ammonium salt of other carboxylated polymers. One preferred dispersant agent is the ammonium polymethylmethacrylate polymer sold by R. T. Vanderbilt under the tradename Darvan 821A. The polymer dispersant is preferably added to the slurry to make up between about 0.2 to 5 percent of the total liquid volume of the slurry.

The slurry may further contain between about 1–5 percent by weight silicon carbide particles, such as obtainable from Washington Mills Electro Minerals Corp. (Niagara Fall, N.Y.).

A preferred method for preparing a slurry of the type just described is detailed as follows. Briefly, heat-treated silica fibers are suspended in water at a preferred fiber:water ratio of about 1:300 to 1:800. The fiber slurry is pumped through a centrifugal cyclone to remove shot glass and other contaminants, such as high soda particles. The fiber cake formed by centrifugation is cut into segments, dried at 550° F. for at least 8 hours, and then broken into smaller chunks for forming the matrix.

Fragments of the silica fiber cake are mixed in a desired weight ratio with alumina fibers, and the fibers are dispersed in an aqueous solution containing the dispersing agent. At this point, the fibers are preferably chopped to a desired average fiber length in a low-shear/high-shear mixer. In general, the greater the degree of chopping, the shorter the fibers, producing better packing and a less open matrix structure. Similarly, longer fibers lead to more open matrix structure. The fiber mixing is preferably carried out under condition to produce average fiber sizes of a selected size in the 1–10 mm fiber-length range.

After mixing, the fibers are allowed to settle, and the liquid/fiber ratio is reduced by decanting off some of the dispersing liquid. To this slurry is added an aqueous gel mixture formed of the viscosity agent, e.g., methyl cellulose, and the matrix particles, e.g., boron nitride particles, and the slurry components are mixed to form the desired high-viscosity slurry. The slurry is now ready to be transferred to a casting mold, to prepare the green-state block, as described in the next section.

C. Forming a Dried Fiber Block

According to an important aspect of the method, the slurry is allowed to settle and is dewatered in a fashion designed to achieve a relatively uniform fiber density throughout the matrix, and relatively randomly oriented fibers, i.e., with little a fiber orientation preference in the direction of settling.

In the first step, a slurry is added to a mold equipped with a lower screen sized to retain slurry fibers. For fiber sizes in the range 1–10 mm, the screen has a mesh size between about 8 to 20 squares/inch. The mold has a lower collection trough equipped with a drain and a vacuum port connected to a suitable vacuum source.

Initially, the slurry is added to the mold and, after stirring the slurry to release gas bubbles, is allowed to settled under gravity, until the level of water in the mold is about 1–2 inches above the level of the desired final compaction height, i.e., the final height of the dewatered block. For a slurry of about 12 1 added to a 18 cm$^2$ square mold, the initial settling takes about 3–10 minutes.

The partially drained slurry in the mold is now compacted with a compacting ram to force additional water from slurry. This is done by allowing the ram to act against the upper surface of the slurry under the force of gravity, while draining the water forced through a screen from the mold. Water is squeezed from the slurry until the ram reaches the desired compaction height. With the slurry volume and mold dimensions just given, a ram having a weight of about 7 lbs is effective to compress the partially dewatered slurry in a period of about 0.2 to 2 minutes.

In the final step of compacting and dewatering, the drain is closed and vacuum is applied to a port until the block is completely dewatered. A vacuum of between about 0.01 to 0.5 atm is effective to produce complete dewatering of the mold in a period of about 0.2 to 5 minutes. The vacuum dewatering may result in the upper surface of the block pulling away from the ram.

The dewatered block is now removed from the mold and dried in an oven, typically at a temperature between 250° F.–500° F. In the dried matrix, the viscosity agent, and to a lesser extent, the dispersant agent, act to bond the fibers at their intersections, forming a rigid, non-fused block. The target density of the matrix after drying is between about 3.3 to 5.3 pounds/ft$^3$.

The green-state matrix may be formed to include sacrificial filler element(s) that will be vaporized during sintering, leaving desired voids in the final fused matrix block. The filler elements are preferably formed of polymer or graphite. An array of parallel rods may be placed in the mold, at the time the slurry is added. Slurry settling and dewatering are as described above, to form the desired green-state block with the included sacrificial element.

The first step is the slurry formation. The slurry may be a single fiber suspension containing a desired size range and fiber composition. Alternatively, for forming a discontinuous or step fiber matrix, two or more slurries having different fiber thicknesses, densities, and/or fiber compositions may be formed.

After the slurry is introduced into the mold, the steps in settling and dewatering the slurry can be varied to produce either a continuous gradient of fiber density or a uniform fiber density. The steps in forming a uniform gradient, including an initial settling step, followed by ram compaction and final dewatering by vacuum have been considered above.

To produce a continuous gradient of fiber densities, the slurry is first subjected by dewatering by vacuum, causing material closest to the screen to be compacted preferentially. When a desired gradient is achieved, the slurry is gravity drained to dewater the slurry, then ram-compacted for further dewatering. The slurry may be subjected to a final vacuum dewatering.

To produce a block having a series of discontinuous layers, each with a uniform fiber density, each successive slurry is handled substantially as described above for the uniform-density block. The layers can be formed by successively casting layer upon layer in the mold, with each successive layer being compacted as described above. Alternatively, a series of block layers, each with a distinctive fiber size/composition and/or density is prepared. Before drying, the individual blocks are placed together in layers, to form the desired discontinuous-layer block. The layers may be "glued" together before drying by applying, for example, a layer of boron nitride in the viscosity agent between the layers.

D. Fused Fiber Matrix

In the final step of matrix formation, the green-state block from above is sintered under conditions effective to produce surface melting and fiber/fiber fusion at the fiber crossings. The sintering is carried out typically by placing the green-state block on a prewarmed kiln car. The matrix is then heated to progressively higher temperature, typically reaching at least 2,000° F., and preferably between about 2,200° F.–2,400° F., until a desired fusion and density are achieved, the target density being between 3.5 and 5.5 pounds/ft$^3$. For a block formed solely of alumina fibers, a maximum temperature of about 2,350° F. is suitable.

In a preferred method, discussed above, the matrix is formed with high-purity silica fibers that contain little or no contaminating boron and/or with alumina fibers that are also substantially free of boron. In order to achieve fiber softening and fusion above 2,000° F., typically in the temperature range 2,000° F.–2,200° F., it is necessary to introduce boron into the matrix during the sintering process, to form a silica/boron or alumina/boron eutectic mixture at the fiber surface. Boron is preferably introduced, as detailed above, by including boron nitride particles in the green-state block, where the particles are evenly distributed through the block.

During sintering, the boron particles are converted to gaseous $N_2$ and boron, with the released boron diffusing into the surface of the heated fibers to produce the desired surface eutectic, and fiber fusion. The distribution of boron particles within the heated block ensures a relatively uniform concentration of boron throughout the matrix, and thus uniform fusion properties throughout.

Also during fusion, the viscosity agent and dispersant agents used in preparing the green-state block are combusted and driven from the block, leaving only the fiber components, and, if added, silicon carbide particles.

Where the green-state block has been constructed to include a sacrificial element, the sintering is also effective to vaporize this element, leaving desired voids in the matrix, such as a lattice of channels throughout the block.

After formation of the fused-fiber matrix, the matrix block may be machined to produce the desired shape and configuration. For example, the matrix can be formed by drilling an array of channels in the block; or by cutting the block into thin plates.

Polymer Fiber Matrix

In another aspect, the invention includes a fibrous polymer matrix. The matrix is composed of fused polymer fibers, and is characterized, in dry form, by: (a) a rigid, three-dimensionally continuous network of open, intercommunicating voids, and (b) a free volume of between about 90–98 volume percent. The fibers may also include up to 80 percent by weight of either silica fibers, alumina fibers, or a combination of the two fibers types.

The matrix is designed for use particularly as a substrate for cell growth in vitro, and as such, contains an array of channels extending through the matrix. In an alternative embodiment, the matrix has a multi-plate configuration.

The fused polymer matrix is formed substantially as described for the silica, alumina, or silica/alumina fiber matrices described above, but with the modifications now to be discussed.

The polymer fibers used in constructing the matrix may be any thermoplastic polymers that can be heat fused, typically when heated in the range 400° F.–800° F. Exemplary polymer fibers include polyimide, polyurethane, polyethylene, polypropylene, polyether urethane, polyacrylate, polysulfone, polypropylene, polyetheretherketone, polyethyleneterphthalate, polystyrene, and polymer coated carbon fibers. Fibers formed of these polymers, and preferably having thickness in the 0.5 to 20 $\mu$m range, can be obtained from commercial sources. The fibers may be chopped, i.e., by shearing, to desired lengths, e.g., in the 0.1 to 2 mm range, by subjecting a suspension of the fibers to shear in a high-shear blender, as described above.

The polymer fibers may be blended with up to 80 weight percent silica and/or alumina fibers of the type described above. Preferably, the silica fibers are heat treated to close up surface imperfections on the fiber surfaces, as described above. The alumina fibers may also be heat treated, e.g., under the sintering conditions described above, to produce surface granulation on the fiber.

The aqueous fiber slurry used in preparing the matrix contains, in addition to fibers, a viscosity agent effective to produce a final slurry viscosity between about 1,000 and 25,000 centipoise. Viscosity agents of the type mentioned above are suitable. If the polymers fibers are relatively hydrophobic, or if the fibers include silica fibers, the slurry should contain a dispersant effective to prevent the fibers from aggregating on settling. Such a dispersant may include surfactants and/or charged polymers, and/or block copolymers, such as polyethylene/polypropylene block copolymers known to enhance the hydrophilicity of polymer surfaces.

The slurry also contains an adhesive agent effect to retain the green-state fiber network in a rigid condition once it is formed. Either the viscosity agent or dispersant may supply the necessary adhesive properties. Alternatively, a separate adhesive component may be added to the slurry.

The above slurry is placed in a settling mold, as above, and the fibers are allowed to settle under dewatering conditions, substantially as described above, to yield randomly oriented fibers having a desired fiber density. The network is formed into a greenstate block by drying, e.g., at 100° F.–300° F.

In the final step, the greenstate block is heated under conditions, typically at a temperature between 400° F.–800° F., effective to produce fiber fusion at the fiber points of intersection. The selected temperature is near the softening point of the thermoplastic polymer. At this temperature, the polymer fibers fuse with one another and with silica and/or alumina fibers in the block to produce the desired rigid, fused fiber matrix.

Utility: Cell-Growth Substrate

The low-density matrix described above in the above sections is designed particularly for use as a substrate for cell growth in vitro, or in vivo as an implantable substrate.

The architecture of the matrix, and particularly the characteristics of a rigid, three-dimensionally continuous network of open, intercommunicating voids, and a free volume of between about 90–98 volume percent, permit rapid cell growth in three dimensions.

In a preferred embodiment, the matrix is formed of silica fibers, typically in an amount between about 50–100 weight percent of the total fiber weight. In another preferred embodiment, the matrix is formed to include alumina fibers, preferably heated to produce surface granulation, in an amount of fiber preferably between about 20–80 weight percent fiber.

The silica and/or alumina fibers may enhance cell adhesion, and/or adhesion of growth factors, such as fibrofectin, vibronectin, or fibrinogen. Representative cell culture and cell implantation applications are discussed below.

A. Cell Culture

In one general embodiment, the matrix of the invention is used to support cell growth in a cell culture system in vitro. A first configuration uses a fiber matrix having a lattice of channels extending through the matrix. The matrix is supported in a culture vessel partially filled with culture medium. The medium is pumped into and through the matrix. The system further includes a filter placed in-line with the pump for extracting desired cell products and/or purifying the medium of cell bi-products. Suitable heating and gas-supply means for maintaining desired gas and temperature control of the medium may also be employed, as well as means for replenishing the medium. A second cell culture configuration utilizes a multi-plate matrix. The plates in the matrix are submerged in a suitable cell culture medium in a vessel, and the medium is circulated, through the plates by a pump. The configuration may also include a filter and culture control means, as indicated above.

In a third configuration, the matrix is present as fragments which are suspended in a culture medium. The matrix fragments are produced preferably by fragmentizing matrix plates of having a thickness between about 0.2 to 2 mm. The matrix fragments, being slightly denser than the culture medium, can be maintained in a suspended state, by gentle stirring or gas bubbling, and can be separated readily from the medium by settling, centrifugation or filtration.

It will be understood that the matrix in the configurations is first sterilized, conventionally, and may be further treated to preabsorb agents which promote cell adhesion to the substrate. Typically these agents include a divalent cation, such as $Mg^{+2}$, and a glycoprotein such as fibronectin, polyethylene, and/or fibrinogen. The pretreatment preferably involves incubating the sterilized matrix in a serum or other medium containing the growth factors of interest.

Alternatively, the fibers, meaning either silica or polymer fibers, may be derivatized by covalent attachment of desired growth factors, such as bone osteogenic factor, cytokines, or the like. Methods for derivatizing the free hydroxyl groups on silica fibers, or free hydroxyl, amine, carboxyl, suldydryl, or aldehyde groups that may be present on polymer fibers are well known.

B. Implantable Cell Matrix

In another general application, the matrix of the invention is used as an implantable substrate for supporting cell growth in vivo. As one example of this application, a hip replacement device having a stem designed to be inserted and locked into the femur of subject, and a ball which will serve as the ball of the repaired hip joint. The stem has a titanium inner core which is formed integrally with the ball. The cover is ensheathed in a fused-fiber matrix constructed according to the invention, and which forms a covering over the core. The matrix covering is preferably formed by machining a fused-fiber block of the type described above. The covering may be attached to the stem core by a suitable adhesive, or by heat fusion near the melt temperature of the titanium, in the case of a silica and/or alumina fiber matrix.

In operation, the matrix on the stem provides a substrate for the growth and infusion of osteoblast cells, acting to weld the stem to the bone through a biological bone structure. The matrix fibers may include bone growth factors for promoting bone cell growth into the matrix.

An implantable cell substrate device can be constructed according to the invention. The device is designed for use as an implantable substrate for supporting growth of a selected tissue cells, such as pancreatic cells or fibroblasts, capable of producing desired cell metabolites such as insulin or interferon.

This device has a tubular construction, and provides a spiraled inner core for supporting cell growth, while allowing body fluids to bathe the cells, bringing nutrients and removing cell products. The device is formed preferably by machining a block of fused-fiber matrix of the type disclosed herein. The outer surface of the device is coated with a biocompatible material, such as silicon rubber to insulate the fiber matrix from direct contact with the surrounding tissue.

In operation, the device is seeded with the desired cells in culture, preferably until the spiraled core has a maximum cell density. The device is then implanted into a desired tissue region, e.g., an intramuscular site.

The two examples described above illustrate two of a variety of implant devices, for bone repair, bone replacement, and tissue-cell augmentation or replacement that may be prepared using the cell-substrate matrix material of the invention.

Utility: Chromatography

The silica-fiber matrix of the invention is also useful for chemical and cell chromatographic separations.

In one embodiment, the matrix can serve as a substrate for thin-layer chromatographic separations, using well-known solvent-systems and development conditions. The matrix in this application is preferably a thin matrix plate, formed, for example, by slicing a matrix block to a desired thickness, e.g., between 1–3 mm. Alternatively, thin plates may be prepared by slurry settling, as described above, in thin-plate molds.

In a related aspect, the matrix serves the role of a silica gel column for chemical separations by silica gel chromatography. As above, the matrix may be machined from a block matrix mold, or formed by settling in a suitable cylindrical mold. For both applications, the density of the matrix is preferably above the 3.5–5.5 pounds/ft$^3$ matrix density that is employed for cell culture.

According to another aspect of the invention, the fused-fiber matrix material having a density between about 3.5 and 5.5 pounds/ft$^3$ is useful for cell-separation chromatography, and typically for use in separating cells and other particles above about 1 micron in size from serum components in a blood sample.

A diagnostic test strip can be prepared for use in detecting a serum components, such as glucose, cholesterol, or a cholesterol-containing lipoprotein, such as low density lipoprotein or high-density lipoprotein particles. The strip, which is formed of the fused-silica fiber matrix material of the invention, includes an application site at one strip end a detection site at the opposite end. The detection site may include reagents for producing a detectable color signal in the presence of a selected serum analyte. Alternatively, serum from this site may be transferred by physical contact to a separate reagent pad.

In operation, a blood sample, e.g., a 25–200$\mu$ sample, is added to the application site, and the sample is drawn by capillarity toward the strip's opposite end. Migration of the sample through the interstices of the matrix acts to retard the migration rate of larger particles, including blood cells, causing separation of the blood cells separated into a slower migrating blood cell fraction and a faster-migrating serum fraction, which is received at the detection site free of blood cells. Analyte detection may occur at this site, or a separate detection pad may be brought in contact with the strip site, to draw serum into the pad.

METHODS OF USE

Drugs or other biologically active materials can be incorporated into the materials, making the materials a drug delivery device. The device can be implanted into an animal. The density of the material and the loading of the drug can be altered in order to modulate the time release property of the device. The drug can be a small molecule organic, a protein, a peptide, a nucleic acid, a growth factor, or any other biologically active substance.

The materials can be used as a filler material. Filler materials can be used to reinforce organic, inorganic, or metallic materials. The filler materials can be used to reinforce polymers. The materials can be used as a composite filler for collagen.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A high density porous composition comprising:
   up to about 100% by weight silica wherein the silica comprises from about 50% to about 100% by weight cristobalite;
   up to about 60% by weight alumina; and
   an additional metal oxide;
   wherein the composition has a density of at least about 12 pounds per cubic foot, a mean pore diameter of about 50 microns to about 600 microns, at least about 50% of the exposed surface area is silicon dioxide, said surface modified by a chemical reaction to increase its hydrophilicity or hydrophobicity.

2. The composition of claim 1, further comprising tantalum oxide or zirconium oxide.

3. The composition of claim 1, further comprising carbon fiber.

4. The composition of claim 1, further comprising a drug.

5. The composition of claim 1, further comprising silica gel.

6. The composition of claim 1, wherein the density is at least about 24 pounds per cubic foot (128 kg/m3).

7. The composition of claim 1, wherein the density is at least about 48 pounds per cubic foot (192 kg/m3).

8. The composition of claim 1, wherein the density is at least about 36 pounds per cubic foot (577 kg/m3).

9. The composition of claim 1, wherein the density is at least about 64 pounds per cubic foot (1025 kg/m3).

10. The composition of claim 1, wherein the exposed surface is at least about 75% silicon dioxide.

11. The composition of claim 1, wherein the exposed surface is at least about 95% silicon dioxide.

12. The composition of claim 5, wherein the silica gel reinforces the composition.

13. The composition of claim 1, wherein the chemical reaction to increase the hydrophilicity or hydrophobicity of the surface area comprises reaction with a hydroxide.

* * * * *